US009593947B2

(12) United States Patent
Tian et al.

(10) Patent No.: US 9,593,947 B2
(45) Date of Patent: *Mar. 14, 2017

(54) METHOD FOR THE MEASUREMENT OF TURBULENCE BY USING RECIPROCATING OCEAN MICROSTRUCTURE PROFILER

(71) Applicant: Ocean University of China, Qingdao (CN)

(72) Inventors: Jiwei Tian, Qingdao (CN); Wei Zhao, Qingdao (CN); Dalei Song, Qingdao (CN); Qingxuan Yang, Qingdao (CN); Ming Xu, Qingdao (CN)

(73) Assignee: OCEAN UNIVERSITY OF CHINA, Qingdao, Shandong (CN)

( * ) Notice: Subject to any disclaimer, the term of this patent is extended or adjusted under 35 U.S.C. 154(b) by 237 days.

This patent is subject to a terminal disclaimer.

(21) Appl. No.: 14/567,049

(22) Filed: Dec. 11, 2014

(65) Prior Publication Data

US 2015/0354956 A1   Dec. 10, 2015

(30) Foreign Application Priority Data

Jun. 9, 2014  (CN) .......................... 2014 1 0252601

(51) Int. Cl.
   *G01C 5/00*      (2006.01)
   *G01D 21/00*     (2006.01)
   *G01C 13/00*     (2006.01)
   *G01N 33/18*     (2006.01)

(52) U.S. Cl.
   CPC ......... *G01C 13/00* (2013.01); *G01N 33/1886* (2013.01)

(58) Field of Classification Search
   USPC ......................................... 73/170.29, 170.34
   See application file for complete search history.

(56) References Cited

U.S. PATENT DOCUMENTS

| 4,924,698 | A | * | 5/1990 | Echert | ..................... B63B 22/18 |
| | | | | | 441/33 |
| 5,644,077 | A | * | 7/1997 | Fowler | ..................... B63B 3/04 |
| | | | | | 73/170.29 |
| 5,869,756 | A | * | 2/1999 | Doherty | ................. B63B 22/18 |
| | | | | | 405/188 |

(Continued)

*Primary Examiner* — Clayton E Laballe
*Assistant Examiner* — Warren K Fenwick
(74) *Attorney, Agent, or Firm* — Buchanan Ingersoll & Rooney PC

(57) ABSTRACT

The method for the measurement of turbulence by using reciprocating ocean microstructure profiler includes the following procedures: 1) system startup; 2) detection of the profile data of ocean dynamic environment information: a. temperature detection; b. shear detection; c. depth detection; and d. current and temperature & conductivity detection; e. gesture sensing; 3) control of ascending and descending operations of the profiler: a. uprising control; b. redirection operation; and c. sinking control; and 4) sleep mode. The method doesn't consume labor several times and the equipment is capable of providing long-time continuous profile measurement at a fixed area along a steel cable; and the entire system can ascend and descend steadily after hydrodynamic optimized layout, eliminating the measurement errors contributable to water flow fluctuation during detection, thus obtaining accurate ocean microstructure observation in vertical with higher precision.

9 Claims, 5 Drawing Sheets

(56) References Cited

U.S. PATENT DOCUMENTS

2008/0087209 A1* 4/2008 Yoshida .................. B63B 22/20
  114/333
2012/0204775 A1* 8/2012 Watanabe ................ B63G 8/24
  114/56.1
2015/0354957 A1* 12/2015 Tian ....................... G01C 13/00
  73/170.29

* cited by examiner

METHOD FOR THE MEASUREMENT OF TURBULENCE BY USING RECIPROCATING OCEAN MICROSTRUCTURE PROFILER

CROSS-REFERENCE TO RELATED APPLICATIONS

The present application claims the priority of CN 201410252601.1, filed in China on Jun. 9, 2014. The present application incorporates by reference the entirety of CN 201410252601.1 and the application filed in the U.S. on even date herewith by the same inventors titled A RECIPROCATING OCEAN MICROSTRUCTURE PROFILER.

TECHNICAL FIELD

The present invention belongs to the technical field of the ocean explorer and relates to an instrument capable of providing all-round ocean exploration and more specifically to a detection method of a reciprocating ocean microstructure profiler.

BACKGROUND

Human cognition and exploration on the ocean can be traced back to the $3^{rd}$ century BC and experienced three processes, i.e., pure commerce & adventure sailing, sailing comprising science meanings and pure scientific expedition based on modern technology. The oceanography is a science based on observation and every leap in the process of cognition on the ocean is based on the advent of a new observation method and measuring instrument. Recalling the history of ocean observations, the advent of the acoustic Doppler current profiler enabled the people to master large-scale circulation structure around the globe, the emergence of the conductivity-temperature-depth (CTD) profiler enabled the people to ascertain the large-scale water mass formation and transformation in the entire ocean, the launch of various satellite altimeters enabled the people to make preliminary cognition on meso-scale and small-scale processes in the ocean such as spatial structure and time evolution of meso-scale eddies and internal waves.

The oceanographic study has made great progress in large-scale and meso-scale processes but scientific study on microscale has just begun. In recent years, the shear, temperature, conductivity probes with high-frequency sampling have been successfully developed in succession, opening the curtain for the study on ocean microscale process. Currently, the measurement methods of ocean microstructure mainly include mooring point measurement method and shipboard vertical profile measurement method. The mooring point measurement method only conducts measurement at a specific depth at a particular fixed position in the ocean, can get better time-series observations but fails to obtain the vertical structure features of the ocean microstructure. The shipboard vertical profile measurement method completes measurements of the ocean microstructures from the surface to a depth by means of an oceanographic vessel, but fails to get the temporal variability of ocean microstructure and is restricted by unfavorable factors such as complicated sea conditions and site operations. For the study on ocean microstructure, time variance and spatial structure are important parameters, based on this, it is urgent to solve the problem of the development and obtainment of an ocean microstructure observation instrument for both vertical spatial structure and time variance.

For the description or the study of ocean microstructure, the turbulent kinetic energy dissipation rate is an important physical variable. Therefore, the direct and accurate measurement is significant to improve the study on turbulent kinetic energy transfer and dissipation. In recent years, the shear probe with high-frequency sampling has been capable of accurately measuring the turbulence kinetic energy dissipation rate, but its application is either based on mooring point measurement or based on shipboard vertical profile measurement and fails to integrate both two measurements. It can be seen that it is of significance to create an innovative method and observation platform to achieve organic integration of the shear probes with high-frequency sampling into both platforms so as to break through the bottleneck of ocean microstructure observation.

SUMMARY OF THE INVENTION

An objective of the present invention is to provide a method for the measurement of turbulence by using reciprocating ocean microstructure profiler for long-term continuous profile observation on the turbulent kinetic energy dissipation rate by means of direct detection with a shear probe through adopting a symmetrical steady structure with a steel cable being secured and placed through penetration in a sea area.

The objective of the present invention can be achieved by the following technical solution: a method for the measurement of turbulence by using reciprocating ocean microstructure profiler. The said reciprocating ocean microstructure profiler comprises the first profiler subunit, the second profiler subunit and a central stand, wherein these two profiler subunits are secured to the left and right sides of the central stand respectively, a steel cable penetration hole for connecting the steel cable to the central stand is provided at the central axis of the central stand and the steel cable longitudinally penetrates the central stand via the steel cable penetration hole, the central stand can slide up and down along the steel cable where an upper limit part and a lower limit part are provided to limit the sliding distance of the central stand, the first profiler subunit is provided with the first buoyancy drive part and the first observation part from top to down, the first buoyancy drive part is provided, from top to bottom, with a floating compartment holding a top oil bladder, a drive compartment holding a bottom oil bladder, and a pressure compartment holding a drive pump assembly and a solenoid valve, the drive pump assembly connects the top oil bladder to the bottom oil bladder via the oil outlet line and the solenoid valve connects the top oil bladder to the bottom oil bladder via the oil return line, the first observation part is electrically connected to the controller which is electrically connected to the drive pump assembly and solenoid valve; the second profiler subunit is provided with the second buoyancy drive part and the second observation part from top to down, the second buoyancy drive part is provided, from top to bottom, with a floating compartment holding a top oil bladder, a drive compartment holding a bottom oil bladder, and a pressure compartment holding a drive pump assembly and a solenoid valve, the drive pump assembly connects the top oil bladder to the bottom oil bladder via the oil outlet line and the solenoid valve connects the top oil bladder to the bottom oil bladder via the oil return line, the second observation part is electrically connected to the controller which is electrically connected to the drive pump assembly and solenoid valve; the said detection method comprises the following procedures:

1) System startup: The said steel cable is located in the sea area in advance and penetrates the central stand of the reciprocating ocean microstructure profiler which slides freely into the deep seawater from top to bottom along the steel cable, the observation units of the first and second profiler subunits are started to detect ocean profile data, and at the same time, the buoyancy drive units in the first and second profiler subunits are started to perform ascending and descending operations of the body.
2) Detection of the profile data of ocean dynamic environment information:
   a. Temperature detection: In the first observation part of the first profiler subunit, the ocean profile temperature is measured by the common temperature detection module and fast temperature detection module located in the temperature probe;
   b. Shear detection: In the first observation part of the first profiler subunit, the high-frequency fluctuating velocity of the current is measured by the shear detection module located in the shear probe and the turbulence kinetic energy dissipation rate is directly derived from the shear value of high-frequency fluctuating velocity;
   c. Depth detection: In the first observation part of the first profiler subunit, the depth of the profiler in water is measured by the pressure detection module located in the depth probe, thus obtaining the descent or ascent rate so as to calculate the turbulence kinetic energy dissipation rate;
   d. Current and temperature & conductivity detection: In the second observation part of the second profiler subunit, the current parameters as well as temperature, conductivity and pressure data are measured by the current sensing module located in the current meter and the thermohaline sensing module located in the CTD profiler respectively;
   e. Gesture sensing: In the first observation part of the first profiler subunit, the gesture and navigation direction of the profiler are measured by the gesture sensing module located in the gesture sensor and the checked three-dimensional acceleration, angular velocity and magnetic density data will also be provided;
3) Control of ascending and descending operations of the profiler:
   a. Uprising control: The main control module located in the controller signals a command via a serial port to the buoyancy drive control module which controls the buoyancy of the two profiler subunits symmetrically arranged on the left and right sides, that is, the operation of the motor is controlled by an H-bridge circuit to drive the high pressure pump to transfer the hydraulic oil from the bottom oil bladder to the top oil bladder so as to achieve uprising of the profiler;
   b. Redirection operation: When each detecting device reaches or is close to its predefined upper limit position, its detected data is constant, and the main control module located in the controller sends a notice via a serial port to the buoyancy drive control module and signals the command of changing from the uprising mode to sinking mode;
   c. Sinking control: The solenoid valve controlled by the buoyancy drive control module is opened and the hydraulic oil in the top oil bladder falls freely back to the bottom oil bladder under hydraulic pressure so as to achieve sinking of the profiler;
4) Sleep mode: When each detecting device reaches or is close to its predefined lower limit position, its detected data is constant, and the main control module located in the controller sends a notice via a serial port to the buoyancy drive control module and signals the command of going to the sleep mode so as to wait for the next startup signal.

The drive pump assembly comprises a motor and high pressure pump, wherein the high pressure pump is connected in series to the oil outlet line and the motor drives and is connected to the high pressure pump via the speed reducer, through which, the started-up motor powers the high pressure pump so as to pump oil from the bottom oil bladder to the top oil bladder. The solenoid valve is connected in series to the oil return line and provided with two lines in parallel, one line is provided with a check valve that prevents hydraulic oil from running from the bottom oil bladder to the top oil bladder via the oil return line and the other is provided with a flow control valve that controls the openness of the valve through controlling the flow to control the oil return flow so as to control the descent rate of the profiler.

In the method for the measurement of turbulence by using reciprocating ocean microstructure profiler, the steel cable is located and placed through penetration in advance in a sea area so as to avoid deploying the steel cable by taking a ship to the surface several times, additionally, the profile survey at the fixed sea area is achieved through several reciprocating operations along the steel cable so as to save labors and achieve long-term, stable and continuous automatic observation on ocean profile. Furthermore, the turbulence kinetic energy dissipation rate can be directly derived from the fluctuating velocity measured by the shear probe so as to achieve long-term continuous profile observation on the turbulence kinetic energy dissipation rate.

In the said method for the measurement of turbulence by using reciprocating ocean microstructure profiler, for the high-frequency gradient signal of the fluctuating velocity measured by the said shear probe, the turbulent kinetic energy dissipation rate, $\epsilon$, can be derived from the observed high-frequency fluctuating velocity shear $$\frac{\partial u_i'}{\partial x_j}$$

in the dissipation sub-range under the assumption of isotropy of turbulence with the following equation:

$$\varepsilon = \frac{1}{2}v\left\langle\frac{\partial u_i'}{\partial x_j}\frac{\partial u_i'}{\partial x_j}\right\rangle = \frac{15}{2}v\int_0^\infty \psi_{obs}(k)dk,$$

where, v refers to coefficient of kinematic viscosity of water, k refers to wavenumber (cpm), $\psi_{obs}(k)$ refers to wavenumber spectrum of fluctuating velocity shear $$\frac{\partial u_i'}{\partial x_j},$$

and angle brackets represent time averaging.

In the said detection method of the reciprocating ocean microstructure profiler, the change, du/dt, of the fluctuating velocity perpendicular to the shear probe axis direction, u, with time, is directly measured by the said shear probe, the vertical shear, $u_z$, of the fluctuating velocity, u, can be obtained through "Taylor's Frozen Turbulence Hypothesis" with the following equation:

$$u_z = \frac{du}{dz} = \frac{1}{W}\frac{du}{dt},$$

where, W refers to the descent rate of the profiler and u refers to the fluctuating quantity of the horizontal velocity.

In the said method for the measurement of turbulence by using reciprocating ocean microstructure profiler, each said detecting device transmits the detection information to the controller which will further sort out and analyze the detection information, complete each ocean microstructure profile measurement and further draw an analysis record chart for each detection information.

In the said method for the measurement of turbulence by using reciprocating ocean microstructure profiler, according to each detection information and data that have been analyzed and sorted out by the said controller, the main control module synchronously transmits the drive command to the buoyancy drive control module which will control the operation of the motor and solenoid valve according to the drive command.

In the said method for the measurement of turbulence by using reciprocating ocean microstructure profiler, the said main control module signals the command of going to the uprising mode to the buoyancy drive control module and synchronously controls the running speed of the motor to control oil discharge flow so as to control the ascent rate of the profiler.

In the said method for the measurement of turbulence by using reciprocating ocean microstructure profiler, the said solenoid valve is provided with two lines in parallel, one line is provided with a check valve that prevents hydraulic oil from running from the bottom oil bladder to the top oil bladder via the oil return line and the other is provided with a flow control valve that controls the openness of the valve during oil return for sinking to control the oil return flow so as to control the descent rate of the profiler.

In the said method for the measurement of turbulence by using reciprocating ocean microstructure profiler, when the said profiler descends to the lower limit position, it stops after suffering elastic buffer impact and then goes to the sleep mode according to the command signal.

Compared with existing techniques, this detection method of the reciprocating ocean microstructure profiler is provided with a steel cable that can be located in and penetrate any sea area profile, eliminating the need for labor every time, so that the equipment automatically provides long-term continuous profile measurement at the fixed area along the steel cable; it adopts integrated symmetrical structure with the center of gravity located below the center of buoyancy, improving the center stability, thus ensuring high stability of the entire system on the hydrodynamic layout; it can achieve the changeover between positive buoyancy and negative buoyancy, steady reciprocating ascending and descending operations and accurate positioning during ascending and descending operations by utilizing the position change of hydraulic oil due to discharge and return; it integrates the CTD profiler, current meter, temperature probe, shear probe, depth probe and gesture sensor, thus achieving all-round ocean microstructure profile measurement, wherein the turbulence kinetic energy dissipation rate can be directly derived from the fluctuating velocity measured by the shear probe so as to achieve long-term continuous profile observation on the turbulence kinetic energy dissipation rate.

In the figures above, 1. steel cable; 2. limit disc; 3. central stand; 4. buffer spring; 5. brush damper; 6. floating compartment; 7. top oil bladder; 8. drive compartment; 9. motor; 10. high pressure pump; 11. solenoid valve; 12. pressure compartment; 13. bottom oil bladder; 14. CTD profiler; 15. current meter; 16. temperature probe; 17. shear probe.

SPECIFIC EMBODIMENTS

Here are the specific embodiments of the present invention and the technical solution of the present invention is further described in reference to the drawings, but the present invention is not limited to these embodiments.

Figure 1:
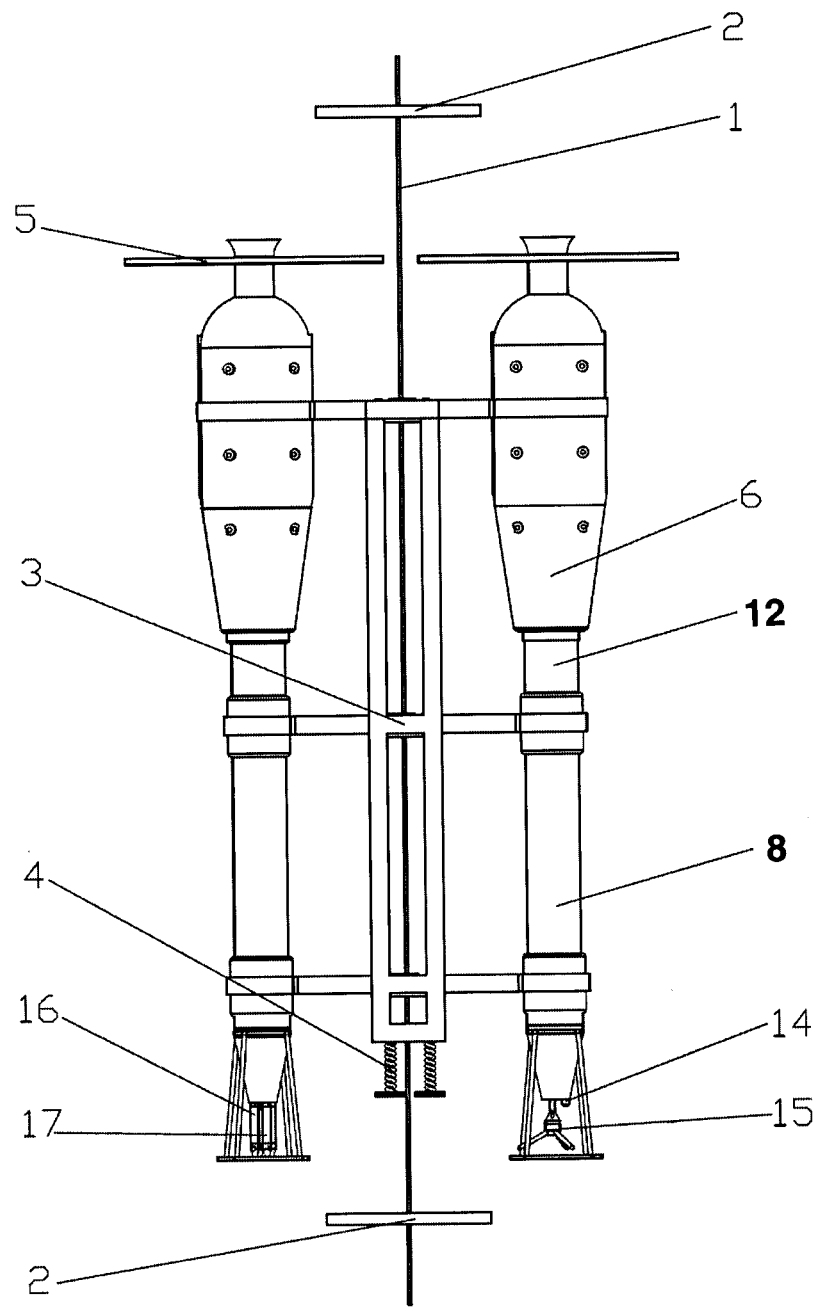
FIG. 1 illustrates an overall structure sketch for the reciprocating ocean microstructure profiler related to the present invention.
Figure 2:
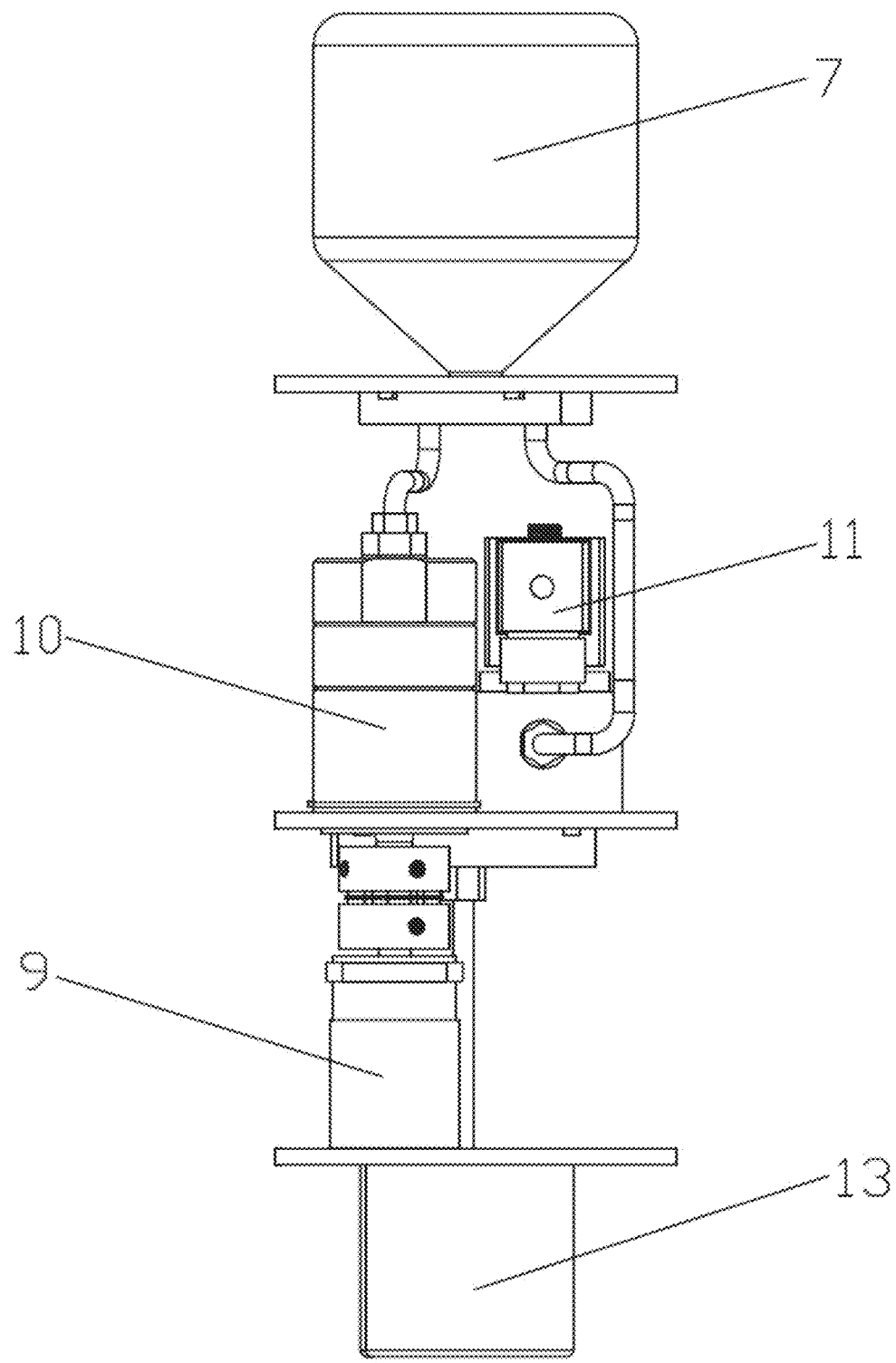
FIG. 2 illustrates a structure sketch for the buoyancy drive part of the reciprocating ocean microstructure profiler related to the present invention.
Figure 3:
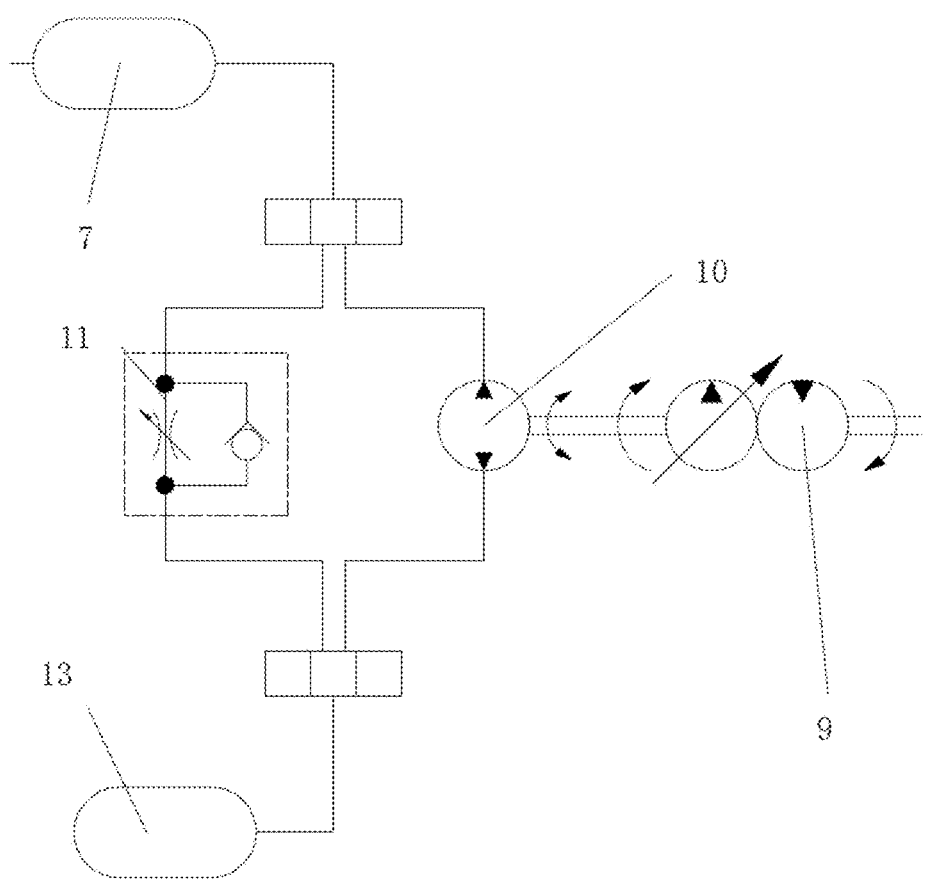
FIG. 3 illustrates a schematic diagram for the buoyancy drive part of the reciprocating ocean microstructure profiler related to the present invention.

As shown in FIGS. 1, 2 & 3, the reciprocating ocean microstructure profiler comprises the first profiler subunit, the second profiler subunit and a central stand 3, wherein these two profiler subunits are secured to the central stand 3, a steel cable penetration hole for connecting the steel cable 1 to the central stand 3 is provided at the central axis of the central stand 3 and the steel cable 1 longitudinally penetrates the central stand 3 via the steel cable penetration hole, the central stand 3 can slide up and down along the steel cable 1 and the steel cable 1 can longitudinally penetrate in any sea area.

The steel cable 1 is sheathed with a plastic surface layer that is favorable to sliding and contact and protects the steel cable 1 against erosion and aging. The upper limit part and lower limit part are provided at the upper and lower limit positions of the steel cable 1 to limit the sliding distance of the central stand 3. Both the upper limit part and lower limit part are limit discs 2 and the steel cable is secured at the center holes of the limit discs 2.

The central stand 3 is provided with a cylindrical frame located at the center, several support sleeves are secured to both sides of the cylindrical frame, and at each side, the upper, middle and lower support sleeves are provided at the upper, middle and lower positions of the first profiler subunit or the second profiler subunit respectively. Several steel cable penetration holes are provided and arranged in the length direction of the cylindrical frame, the circumferential pulleys are provided at the upper and lower ends of each steel cable penetration hole and the steel cable passes through the steel cable penetration holes and connected with the circumferential pulleys in a sliding fashion.

A buffer spring 4 located at the bottom of the central stand 3 will receive elastic buffer impact with the limit disc 2 at the bottom when the central stand 3 descends to the lower limit position. Under the elastic buffer function of the buffer spring 4, impact is reduced so as to avoid damages when the profiler reaches the lower limit position to avoid damages.

The brush dampers 5 are located at the tops of the first profiler subunit and the second profiler subunit and provided with several brush blades that are arranged uniformly in a radial form. When the whole profiler makes ascending and descending motions in the sea water, the brush damper 5 can reduce resistance.

The first profiler subunit is provided with the first buoyancy drive part and the first observation part from top to down, the first buoyancy drive part is provided, from top to bottom, with a floating compartment 6 holding a top oil bladder 7, a drive compartment 8 holding a bottom oil bladder 13, and a pressure compartment 12 holding a drive pump assembly and a solenoid valve 11. An oil outlet line and an oil return line are provided in the drive compartment 8 to form a circulation loop that connects the top oil bladder 7 and the bottom oil bladder 13. The drive pump assembly comprises a motor 9 and high pressure pump 10, wherein the high pressure pump 10 is connected in series to the oil outlet line and the motor 9 drives and is connected to the high pressure pump 10 via the speed reducer, through which, the started-up motor 9 powers the high pressure pump 10 so as to pump oil from the bottom oil bladder 13 to the top oil bladder 7. The solenoid valve 11 is connected in series to the oil return line and provided with two lines in parallel, one line is provided with a check valve that prevents hydraulic oil from running from the bottom oil bladder 13 to the top oil bladder 7 via the oil return line and the other is provided with a flow control valve that controls the openness of the valve through controlling the flow to control the oil return flow so as to control the descent rate of the profiler. The first observation part is electrically connected to the controller which is electrically connected to the motor 9 in the drive pump assembly and the solenoid valve 11.

The second profiler subunit is provided with the second buoyancy drive part and the second observation part from top to down, the second buoyancy drive part is provided, from top to bottom, with a floating compartment 6 holding a top oil bladder 7, a drive compartment 8 holding a bottom oil bladder 13, and a pressure compartment 12 holding a drive pump assembly and a solenoid valve 11. An oil outlet line and an oil return line are provided in the drive compartment 8 to form a circulation loop that connects the top oil bladder 7 and the bottom oil bladder 13. The drive pump assembly comprises a motor 9 and high pressure pump 10, wherein the high pressure pump 10 is connected in series to the oil outlet line and the motor 9 drives and is connected to the high pressure pump 10 via the speed reducer, through which, the started-up motor 9 powers the high pressure pump 10 so as to pump oil from the bottom oil bladder 13 to the top oil bladder 7. The solenoid valve 11 is connected in series to the oil return line and provided with two lines in parallel, one line is provided with a check valve that prevents hydraulic oil from running from the bottom oil bladder 13 to the top oil bladder 7 via the oil return line and the other is provided with a flow control valve that controls the openness of the valve through controlling the flow to control the oil return flow so as to control the descent rate of the profiler. The second observation part is electrically connected to the controller which is electrically connected to the motor 9 in the drive pump assembly and the solenoid valve 11.

The first observation part comprises the temperature probe 16, shear probe 17 and depth probe located at the bottom of the first profiler subunit and the second observation part comprises the CTD profiler 14, current meter 15 and gesture sensor located at the bottom of the second observation part, wherein the turbulence kinetic energy dissipation rate can be directly derived from the fluctuating velocity of the current measured by the shear probe 17. All detecting devices in the first observation part and the second observation part are connected via circuits to the controller where a battery and a turbulence detection circuit that detects and analyzes all detection information are provided.

Figure 4:
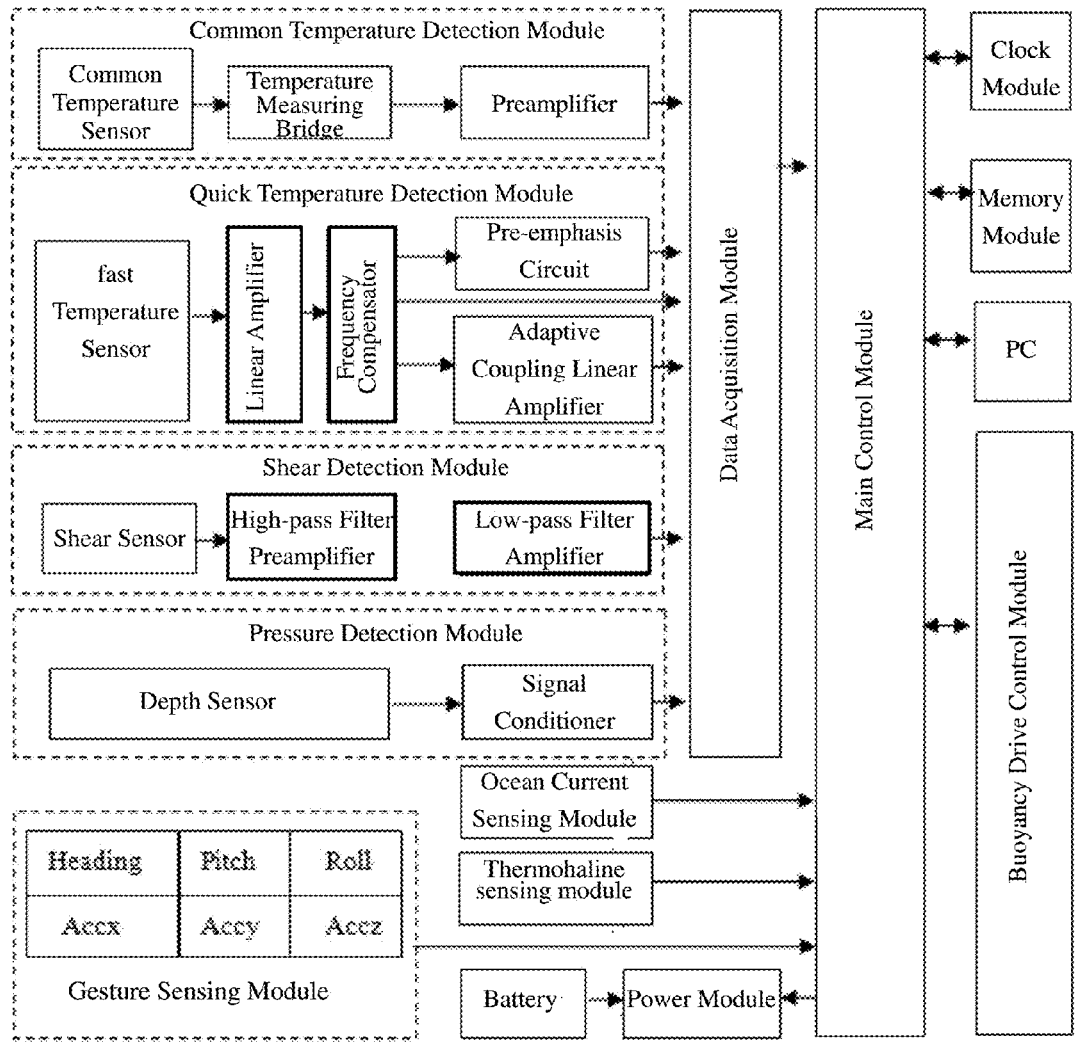
FIG. 4 illustrates a schematic diagram for the internal module structure of the controller in the reciprocating ocean microstructure profiler related to the present invention.

As shown in FIG. 4, the controller holds a main control module with several information receiving ports and a data acquisition module. The temperature probe 16 is provided with a common temperature detection module comprising the common temperature sensor, temperature measuring bridge and preamplifier that are connected in series and a fast temperature detection module comprising the fast temperature sensor, linear amplifier and frequency compensator that are connected in series and the pre-emphasis circuit and adaptive coupling linear amplifier that are connected as branches with the frequency compensator; the shear probe 17 is provided with a shear detection module comprising the shear sensor, high-pass filter preamplifier and low-pass filter amplifier that are connected in series; the depth probe is provided with a pressure detection module comprising the depth sensor and signal conditioner that are connected in series. The common temperature detection module, fast temperature detection module, shear detection module and pressure detection module are connected to the information receiving ports of the main control module via the data acquisition module. The current meter 15 is provided with a current sensing module, the CTD profiler 14 is provided with a thermohaline sensing module, the gesture sensor is provided with a gesture sensing module and these three modules are connected to the information receiving ports of the main control module respectively.

The controller also holds a buoyancy drive control module, clock module, memory module, PC and power module. The main control module communicates mutually with the clock module, memory module, PC and buoyancy drive control module and is connected with the power module which is connected with a battery.

For the reciprocating ocean microstructure profiler, the profiler makes ascending and descending motions in the water depth range of 800 m to 2500 m along the steel cable; its platform moves at a speed of 0.2 m/s~0.3 m/s; its sampling frequency may be set to maximum value 1024 Hz; its controller has a memory capacitance not less than 8 G. In order to ensure the stable gesture of the profiler in the water, the center of gravity is designed to be located below the center of buoyancy, thus improving the center stability; furthermore, a structure that is fully symmetrical in appearance at the left and right sides is adopted to achieve adjustment of the center of gravity so that the center of buoyancy at both sides are identical and the center of gravity at both sides are also the same, ensuring the center of buoyancy and the center of gravity are on the geometrical axis of the profiler, thus ensuring high stability of the entire system on the hydrodynamic layout.

Figure 5:
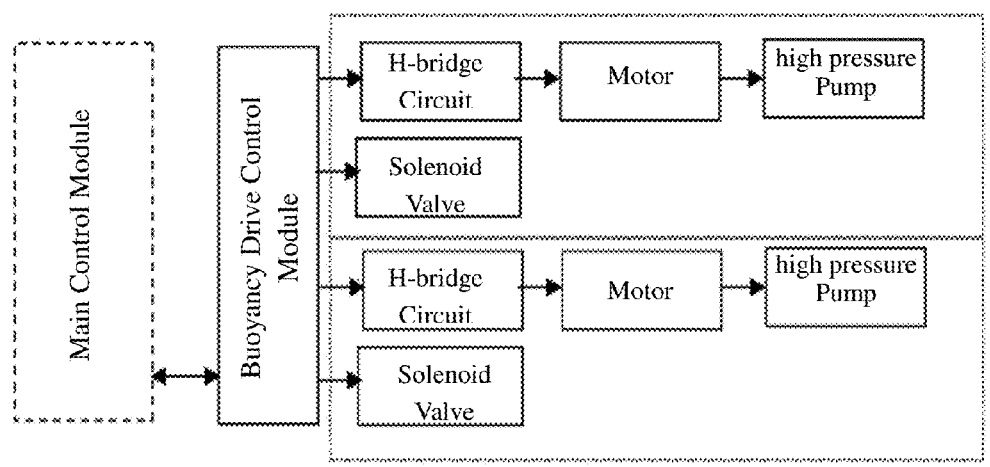
FIG. 5 illustrates a block diagram for the buoyancy drive part of the reciprocating ocean microstructure profiler related to the present invention.

As shown in FIG. 5, the method for the measurement of turbulence by using reciprocating ocean microstructure profiler comprises the following procedures:

1) System startup: The steel cable 1 is located and placed through penetration in the sea area in advance and attached with a profiler, and enables the profiler to slide freely into the deep seawater from top to bottom, each detecting device on the profiler is started to detect ocean profile data and the drive pump assembly and the solenoid valve 11 in the profiler are started and opened to perform ascending and descending operations of the body.

2) Detection of the profile data of ocean dynamic environment information:
   a. Temperature detection: The ocean profile temperature is measured by the common temperature detection module and fast temperature detection module located in the temperature probe 16;
   b. Shear detection: The high-frequency fluctuating velocity of the current is directly measured by the shear detection module located in the shear probe 17 and the turbulence kinetic energy dissipation rate is directly derived from the shear value of high-frequency fluctuating velocity;
   c. Depth detection: The depth of the profiler in water is measured by the pressure detection module located in the depth probe, thus obtaining the descent or ascent rate so as to calculate the turbulence kinetic energy dissipation rate;
   d. Current and temperature & conductivity detection: The current parameters as well as temperature, conductivity and pressure data are measured by the current sensing module located in the current meter 15 and the thermohaline sensing module located in the CTD profiler 14 respectively;
   e. Gesture sensing: The gesture and navigation direction of the profiler are measured by the gesture sensing module located in the gesture sensor and the checked three-dimensional acceleration, angular velocity and magnetic density data will also be provided;

3) Control of ascending and descending operations of the profiler:
   a. Uprising control: The main control module located in the controller signals a command via a serial port to the buoyancy drive control module which controls the buoyancy of the two profiler subunits symmetrically arranged on the left and right sides, that is, the operation of the motor 9 is controlled by an H-bridge circuit to drive the high pressure pump 10 to transfer the hydraulic oil from the bottom oil bladder 13 to the top oil bladder 7 so as to achieve uprising of the profiler;
   b. Redirection operation: When each detecting device reaches or is close to its predefined upper limit position, its detected data is constant, and the main control module located in the controller sends a notice via a serial port to the buoyancy drive control module and signals the command of changing from the uprising mode to sinking mode;
   c. Sinking control: The solenoid valve 11 controlled by the buoyancy drive control module is opened and the hydraulic oil in the top oil bladder 7 falls freely back to the bottom oil bladder 13 under hydraulic pressure so as to achieve sinking of the profiler;

4) Sleep mode: When each detecting device reaches or is close to its predefined lower limit position, its detected data is constant, and the main control module located in the controller sends a notice via a serial port to the buoyancy drive control module and signals the command of going to the sleep mode so as to wait for the next startup signal.

The change, du/dt, of the fluctuating velocity perpendicular to the shear probe 17 axis direction, u, with time, is directly measured by the shear probe 17, the vertical shear, $u_z$, of the fluctuating velocity, u, can be obtained through "Taylor's Frozen Turbulence Hypothesis" with the following equation:

$$u_z = \frac{du}{dz} = \frac{1}{W}\frac{du}{dt},$$

where, W refers to the descent rate of the profiler and u refers to the fluctuating quantity of the horizontal velocity.

For the high-frequency gradient signal of the fluctuating velocity measured by the shear probe 17, the turbulence kinetic energy dissipation rate, $\epsilon$, can be derived from the observed high-frequency fluctuating velocity shear $$\frac{\partial u'_i}{\partial x_j}$$

in the dissipation sub-range under the assumption of isotropy of turbulence with the following equation:

$$\varepsilon = \frac{1}{2}v\left\langle\frac{\partial u'_i}{\partial x_j}\frac{\partial u'_i}{\partial x_j}\right\rangle = \frac{15}{2}v\int_0^\infty \psi_{obs}(k)dk,$$

where, v refers to coefficient of kinematic viscosity of water, k refers to wavenumber (cpm), $\psi_{obs}(k)$ refers to wavenumber spectrum of fluctuating velocity shear $$\frac{\partial u'_i}{\partial x_j},$$

and angle brackets represent time averaging.

In actual data processing, since the sampling frequency of the instrument and the spatial resolution of the shear probe 17 are limited, there is large noise particularly in high-frequency circuits and the signal to noise ratio of the signal is reduced, the equation $$\varepsilon = \frac{1}{2}v\left\langle\frac{\partial u'_i}{\partial x_j}\frac{\partial u'_i}{\partial x_j}\right\rangle = \frac{15}{2}v\int_0^\infty \psi_{obs}(k)dk$$

only can integrate the observed wavenumber spectrum $\psi_{obs}(k)$ in a certain wavenumber range, this is a step iteration process and its basic calculation process is as follows:

(a) Remove the singular values of the velocity shear, $u_z$, and conduct frequency spectrum analysis to obtain its power spectrum $\phi_{obs}(f)$;

(b) In the descent process of the turbulence profiler, like the ocean hybrid fixed-point observation unit, the vibration of the instrument platform will contaminate the shear signal measurement to some extent, so motion compensation correction shall be provided for the fluctuating velocity spectrum through platform acceleration signal a monitored by the acceleration sensor.

The motion compensation correction method is as follows: firstly, prepare the cross spectrum $\phi_{sa}(\omega)$ of signal s and signal a with the equation: $\phi_{sa}(\omega)=F_s(\omega)F_a^*(\omega)$, where, $\omega$ refers to circular frequency; $F(\omega)$ refers to Fourier transform of the signal, * represents being conjugated, and the power spectrum of the signal a is $\phi_{aa}(\omega)$. The correction method is as follows: $\phi'(\omega)=\phi(\omega)(1-R_{sa}^2(\omega))$, where, $$R_{sa}^2(\omega) = \frac{\varphi_{sa}(\omega) * \varphi_{sa}^*(\omega)}{\varphi(\omega)\varphi_{GG}(\omega)},$$

$\phi'(\omega)$ refers to corrected power spectrum which is then converted to frequency spectrum with the equation: $\phi'_{obs}(f)=2\pi\phi'(\omega)$.

(c) The power spectrum $\phi_{obs}'(f)$ is converted to the wavenumber spectrum $\omega_{obs}(k)$ with the equation: $\omega_{obs}(k)=\phi'_{obs}(f)U$;

(d) Since it is impossible that the shear probe 17 is infinitely small, the probe room response correction shall be provided for the wavenumber spectrum $\omega_{obs}(k)$ and the corrected wavenumber spectrum is still expressed as $\psi_{obs}(k)$;

(e) Owing to limited sampling frequency of the instrument and such influences as noises generated from high-frequency circuits, only the turbulence dissipation spectrum in a limited wavenumber sub-range $[k_{min}, k_{max}]$ can be resolved through observation, the dissipation rate is calculated by fitting the observed dissipation spectrum $\psi_{obs}(k)$ and the theoretical Nasmyth spectrum $\psi_{theory}(k)$ with the equation:

$$\varepsilon = \frac{15}{2}v\int_{k_{min}}^{k_{max}}\psi_{obs}(k)dk = \frac{15}{2}v\int_{k_{min}}^{k_{max}}\psi_{theory}(k)dk,$$

where, $k_{min}=1$ $k_{max}=15$ which are assumed as initial values firstly. The Kolmogorov wavenumber $k_s$ is calculated with the equation:

$$k_s = \frac{1}{2\pi}(\varepsilon/v^3)^{1/4};$$

(f) Let $k_{max}=k_s$, repeat calculation step (e), expand the integral interval through continuous iteration and calculate $\epsilon$ and $k_s$. If $k_{max} \geq k_s$, terminate the iteration process.

(g) Integrate the theoretical Nasmyth spectrum obtained from the final iteration in step (f) to calculate the turbulence kinetic energy dissipation rate, $\epsilon$.

Each detecting device transmits the detection information to the controller which will further sort out and analyze the detection information, complete each ocean microstructure profile measurement and further draw an analysis record chart for each detection information. According to each detection information and data that have been analyzed and sorted out by the said controller, the main control module transmits the drive command to the buoyancy drive control module which will control the operation of the motor 9 and solenoid valve 11 according to the drive command. The main control module signals the command of going to the uprising mode to the buoyancy drive control module and synchronously controls the running speed of the motor 9 to control oil discharge flow so as to control the ascent rate of the profiler. The solenoid valve 11 is provided with two lines in parallel, one line is provided with a check valve that prevents hydraulic oil from running from the bottom oil bladder 13 to the top oil bladder 7 via the oil return line and the other is provided with a flow control valve that controls the openness of the valve during oil return for sinking to control the oil return flow so as to control the descent rate of the profiler.

The specific embodiments described herein only explain the spirit of the present invention as examples. The technologists in the technical field of the present invention may make various modifications to or similar replacements for the specific embodiments described herein but such modifications or replacements shall not deviate from the spirit of the present invention or exceed the scope defined in the attached claims.

Although following terms are used many times in the document: steel cable 1; limit disc 2; central stand 3; buffer spring 4; brush damper 5; floating compartment 6; top oil bladder 7; drive compartment 8; motor 9; high pressure pump 10; solenoid valve 11; pressure compartment 12; bottom oil bladder 13; CTD profiler 14; current meter 15; temperature probe 16; shear probe 17 and so on, the possibility of using other terms is not eliminated. The foregoing terms are used only for describing and explaining the essence of the present invention more conveniently; construing them as any additional restriction conflicts with the spirit of the present invention.

What is claimed is:

1. A method for the measurement of turbulence using a reciprocating ocean microstructure profiler, wherein the profiler comprises:
   a first profiler subunit,
   a second profiler subunit, and
   a central stand having a central axis,
   a cable,
   a controller,
   wherein the first and second profiler subunits are secured to opposite sides of the central stand, respectively,
   a cable penetration hole for connecting the cable to the central stand is provided at the central axis of the central stand to enable the cable to longitudinally penetrate the central stand via the cable penetration hole, and the central stand is configured to slide up and down along the cable,
   an upper limit part and a lower limit part are provided on the cable to limit the sliding distance of the central stand,
   the first profiler subunit is provided with a first buoyancy drive part and a first observation part,
   the first buoyancy drive part is configured to perform ascending and descending operations of the profiler, and is provided with a first floating compartment holding a first top oil bladder, a first drive compartment holding a first bottom oil bladder, and a first pressure compartment holding a first drive pump assembly and a first solenoid valve,
   the first drive pump assembly connects the first top oil bladder to the first bottom oil bladder via a first oil outlet line,
   the first solenoid valve connects the first top oil bladder to the first bottom oil bladder via a first oil return line,
   the first observation part is electrically connected to the controller, which is electrically connected to the first drive pump assembly and the first solenoid valve,
   the second profiler subunit is provided with a second buoyancy drive part and a second observation part,
   the second buoyancy drive part is configured to perform ascending and descending operations of the profiler, and is provided with a second floating compartment holding a second top oil bladder, a second drive compartment holding a second bottom oil bladder, and a second pressure compartment holding a second drive pump assembly and a second solenoid valve, the second drive pump assembly connects the second top oil bladder to the second bottom oil bladder via a second oil outlet line, the second solenoid valve connects the second top oil bladder to the second bottom oil bladder via a second oil return line, the second observation part is electrically connected to the controller which is electrically connected to the second drive pump assembly and the second solenoid valve, the first observation part includes:
- a temperature probe having a common temperature detection module and a fast temperature detection module,
- a shear probe having a shear detection module for detecting a high-frequency fluctuating velocity of the current, wherein a turbulent kinetic energy dissipation rate is directly derived from a shear value of the high-frequency fluctuating velocity, and
- a depth probe having a pressure detection module for measuring a depth of the profiler in water is measured by a pressure detection module located in the depth probe, thus obtaining a descent or ascent rate so as to calculate the turbulent kinetic energy dissipation rate, the second observation part includes:
- a current meter having a current sensing module to measure temperature, conductivity and pressure data, and
- a thermohaline sensing module located in a conductivity-temperature-depth (CTD) profiler, wherein the controller is configured to control ascending and descending operations of the profiler by controlling transfer of hydraulic oil from the first and second bottom oil bladders to the first and second top oil bladders, respectively, and the controller is also configured to generate a go to sleep mode command when each detecting device reaches or is close to its predefined lower limit position so as to wait for a next startup signal, wherein the method comprises:

connecting the cable through the cable penetration hole to the central stand to enable the central stand to slide up and down along the cable, performing ascending and descending operations of the profiler with the first and second buoyancy drive parts, measuring an ocean temperature profile by the temperature probe, detecting the high-frequency fluctuating velocity of the current, wherein the turbulent kinetic energy dissipation rate is directly derived from the shear value of high-frequency fluctuating velocity, detecting a depth of the profiler in water by the pressure detection module located in the depth probe, thus obtaining the descent or ascent rate and calculating the turbulent kinetic energy dissipation rate, measuring temperature, conductivity and pressure data, and controlling ascending and descending operations of the profiler by controlling transfer of hydraulic oil from the first and second bottom oil bladders to the first and second top oil bladders, respectively, and generating a go to sleep mode command when each detecting device reaches or is close to its predefined lower limit position so as to wait for the next startup signal.

2. The method according to claim 1, wherein the controller is further configured to:

signal a command via a serial port to a buoyancy drive control module which controls a buoyancy of the two profiler subunits so that the buoyancy is controlled by an H-bridge circuit to drive the first and second drive pumps to transfer the hydraulic oil from the bottom oil bladders to the top oil bladders so as to achieve uprising of the profiler, when a depth is determined to be at or close to a predefined upper limit position, send a notice via a serial port to the buoyancy drive control module and signals the command of changing from an uprising mode to a sinking mode, and signal a command via a serial port to the buoyancy drive control module which controls the buoyancy of the two profiler subunits to transfer the hydraulic oil from the top oil bladders to the bottom oil bladders so as to achieve sinking of the profiler.

3. The method according to claim 2, wherein, for a high-frequency gradient signal of the fluctuating velocity measured by the said shear probe, the turbulent kinetic energy dissipation rate, $\epsilon$, can be derived from the observed high-frequency fluctuating velocity shear $$\frac{\partial u'_i}{\partial x_j}$$

in the dissipation sub-range under the assumption of isotropy of turbulence with the following equation:

$$\varepsilon = \frac{1}{2}v\left\langle\frac{\partial u'_i}{\partial x_j}\frac{\partial u'_i}{\partial x_j}\right\rangle = \frac{15}{2}v\int_0^\infty \psi_{obs}(k)dk,$$

where, v refers to coefficient of kinematic viscosity of water, k refers to wavenumber, $\psi_{obs}(k)$ refers to wavenumber spectrum of fluctuating velocity shear $$\frac{\partial u'_i}{\partial x_j},$$

and angle brackets represent time averaging.

4. The method according to claim 3, wherein a change, du/dt, of the fluctuating velocity perpendicular to the shear probe axis direction, u, with time, is directly measured by the said shear probe, the vertical shear, $u_z$, of the fluctuating velocity, u, can be obtained through "Taylor's Frozen Turbulence Hypothesis" with the following equation:

$$u_z = \frac{du}{dz} = \frac{1}{W}\frac{du}{dt},$$

where, W refers to the descent rate of the profiler and u refers to the fluctuating component of the horizontal velocity.

5. The method according to claim 2, wherein each detecting device transmits the detection information to the controller which will further sort out and analyze the detection information, complete each ocean microstructure profile measurement and further draw an analysis record chart for each detection information.

6. The method according to claim 5, wherein, according to each detection information and data that have been analyzed and sorted out by the said controller, the main control module synchronously transmits the drive command to the buoyancy drive control module which will control the operation of the motor and solenoid valve according to the drive command.

7. The method according to claim 2, wherein said controller signals the command of going to the uprising mode to the buoyancy drive control module and synchronously controls the running speed of the motor to control oil discharge flow so as to control the ascent rate of the profiler.

8. The method according to claim 2, wherein said solenoid valve is provided with two lines in parallel, one line is provided with a check valve that prevents hydraulic oil from running from the bottom oil bladder to the top oil bladder via the oil return line and the other is provided with a flow control valve that controls the openness of the valve during oil return for sinking to control the oil return flow so as to control the descent rate of the profiler.

9. The method according to claim 2, wherein when the said profiler descends to the lower limit position, it stops after suffering elastic buffer impact and then goes to the sleep mode according to the command signal.

* * * * *